United States Patent [19]

Lehtikoski et al.

[11] Patent Number: 4,678,325
[45] Date of Patent: Jul. 7, 1987

[54] APPARATUS FOR MEASURING OPTICAL PROPERTIES OF PAPER

[76] Inventors: Olavi Lehtikoski, Sölvenkatu 8, SF-78300 Varkaus 30; Martti Nissinen, SF-78880 Kuvansi, both of Finland

[21] Appl. No.: 603,512

[22] Filed: Apr. 24, 1984

[30] Foreign Application Priority Data

May 5, 1983 [FI] Finland .................. 831543

[51] Int. Cl.⁴ .................. G01J 3/32; G01N 21/86
[52] U.S. Cl. ........................... 356/73; 356/334
[58] Field of Search ............ 356/73, 405–406, 356/432–435, 326, 328–329, 429–431, 71, 408; 162/263, 49; 364/526

[56] References Cited

U.S. PATENT DOCUMENTS

| | | | |
|---|---|---|---|
| 3,762,817 | 10/1973 | Harklau | 356/73 |
| 3,936,189 | 2/1976 | DeRemigis | 356/73 |
| 4,015,904 | 4/1977 | DeRemigis | 356/429 X |
| 4,084,906 | 4/1978 | Bibbero | 356/326 |
| 4,222,064 | 9/1980 | Lodzinski | 356/429 X |
| 4,243,319 | 1/1981 | Lodzinski | 356/73 |
| 4,279,511 | 7/1981 | Maute et al. | 356/328 |
| 4,439,038 | 3/1984 | Mactaggart | 356/408 |
| 4,565,444 | 1/1986 | Mactaggart | 356/73 |

*Primary Examiner*—Vincent P. McGraw
*Attorney, Agent, or Firm*—Cohen, Pontani & Lieberman

[57] ABSTRACT

The available equipment for measuring optical properties of paper are inconvenient in use and calibration thereof is inaccurate. In addition, properties of a sample are not analyzed sufficiently. According to the invention, a background screen (2) of an apparatus is adapted to be displaced relative to housing (1) and provided with elements (17–21) for measuring optical properties and calibrating said apparatus. In addition, an assembly (9–15) for processing scattered light comprises a grid (13) and at least one limiter (15), positioned between detector (16) and grid in the immediate proximity of detector and adapted to be movable along with detector over the entire range of a spectrum.

12 Claims, 5 Drawing Figures

APPARATUS FOR MEASURING OPTICAL PROPERTIES OF PAPER

The present invention relates to an apparatus for measuring optical properties of paper, said apparatus comprising a housing, inside the housing a background screen, a light source, lenses for focusing light on the background screen or on a paper sample placed on the background screen, detectors for measuring the intensities of reflected and penetrated light, a scattered light processing assembly, as well as a detector for measuring the intensity of scattered light.

At present, the most commonly measured optical properties of paper are factors for representing appearance, such as color, whiteness and gloss as well as factors important for printable paper, such as capacity and transparency. However, calibration of presently available equipment is inconvenient and problematic which is why errors are commonplace. In addition, the determination of chromaticity coordinates generally involves the use of three filters and reading the values corresponding to thus separated wavelengths. The aim striven for by the use of filters is that the common shape of the output curves of filters and detectors corresponds as accurately as possible to the shape of X,Y,Z curves of C.I.E. standard, so that the final X, Y and Z components will obtained by single standard coefficients from measuring results. However, a color definition requires analysis of the entire visible wavelength range and, thus, results obtained with such equipment do not accurately comply with reality.

An object of the invention is to provide an apparatus capable of eliminating some of the drawbacks of the available equipment for measuring optical properties of paper. A further object of the invention is to provide an apparatus which is easy to calibrate and operate. Another object of the invention is to provide an apparatus capable of measuring the entire spectrum of light emitting from a sample.

The object of this invention is achieved by means of an apparatus substantially characterized by what is set out in the annexed claims.

According to the invention, a background screen on which the light coming from a light source is focused is adapted to be displaceable relative to a housing and fitted with means for measuring optical properties and for calibration of said apparatus, and an assembly for processing scattered light comprises a grid and at least one limiter, mounted between detector and grid immediately adjacent to detector and adapted to be displaceable along with said detector within the spectral range, the detector being adapted to measure step by step the intensity of sections of desired width of the spectrum of light at a desired density. Such an apparatus can be readily calibrated and various optical properties of paper can be measured in a simple fashion. The same apparatus is used to measure the intensity values of various wavelengths of scattered light over the spectral range of light, the results matching as accurately as possible the C.I.E. standard.

According to the invention, between grid and detector is preferably disposed a lens for focusing a spectrum, the focal plane being thus provided with focal points in accordance with various wavelengths. Hence, a detector is displaced on focal plane and adjacent thereto, said detector measuring the values of the focal point array (spectrum) of wavelength groups forming on this focal plane and arriving at various angles. The limiter of a detector is provided with a gap of a desired width, preferably as narrow as possible. The gap serves as a bandpass filter, in other words, the passband narrows as the gap is made smaller.

In one preferred embodiment of the invention, the apparatus comprises two gap-equipped plates, disposed between grid and detector adjacent to said detector and serving as limiters. By setting two gaps of equal width in series, the edge sharpness of a filter is improved. The edge sharpness then depends also on the distance between said gaps. In this type of apparatus, a detector and its plates are moved along a curved path according to focal plane.

According to the invention, the apparatus preferably comprises lenses for converging and focusing scattered light as well as an aperture disc or mask, positioned in a manner that the aperture of said aperture disc is in alignment with the focal point of the latter lens. For accurate assembly of the spectrum of light emitting from a paper sample in scattering fashion, the light to be measured is collected as accurately as possible from the illuminated area of an entire target and is re-focused by means of a lens into a point as small as possible. The smaller a point achieved, the more accurate a spectrum will be measured. The aperture of an aperture disc aligned with the light point achieved by lenses provides a target representing, re-constituted light source, all light rays emitting therefrom out of the same focused point and plane. This is significant in view of the later processing of light. Such light converging and refocusing optics is highly preferable in terms of intensity efficiency. In addition, the light to be measured is collected perpendicularly to the plane of a target (paper). At this angle, the portion of directly reflected light is as small as possible.

The apparatus comprises, according to the invention, preferably a collimator, so positioned that its focal point is in register with the aperture of an aperture disc and adapted to direct the light emitting through said aperture as parallel rays to the grid. The light arriving at an optical grid must be accurately parallel over the entire useful area of a grid. A collimator collects the light energy emitting through the aperture and leads it to a grid as parallel rays.

BRIEF DESCRIPTION OF THE DRAWINGS

The invention will now be described in more detail with reference made to the accompanying drawing, in which.

DESCRIPTION OF THE PREFERRED EMBODIMENTS

Figure 1:
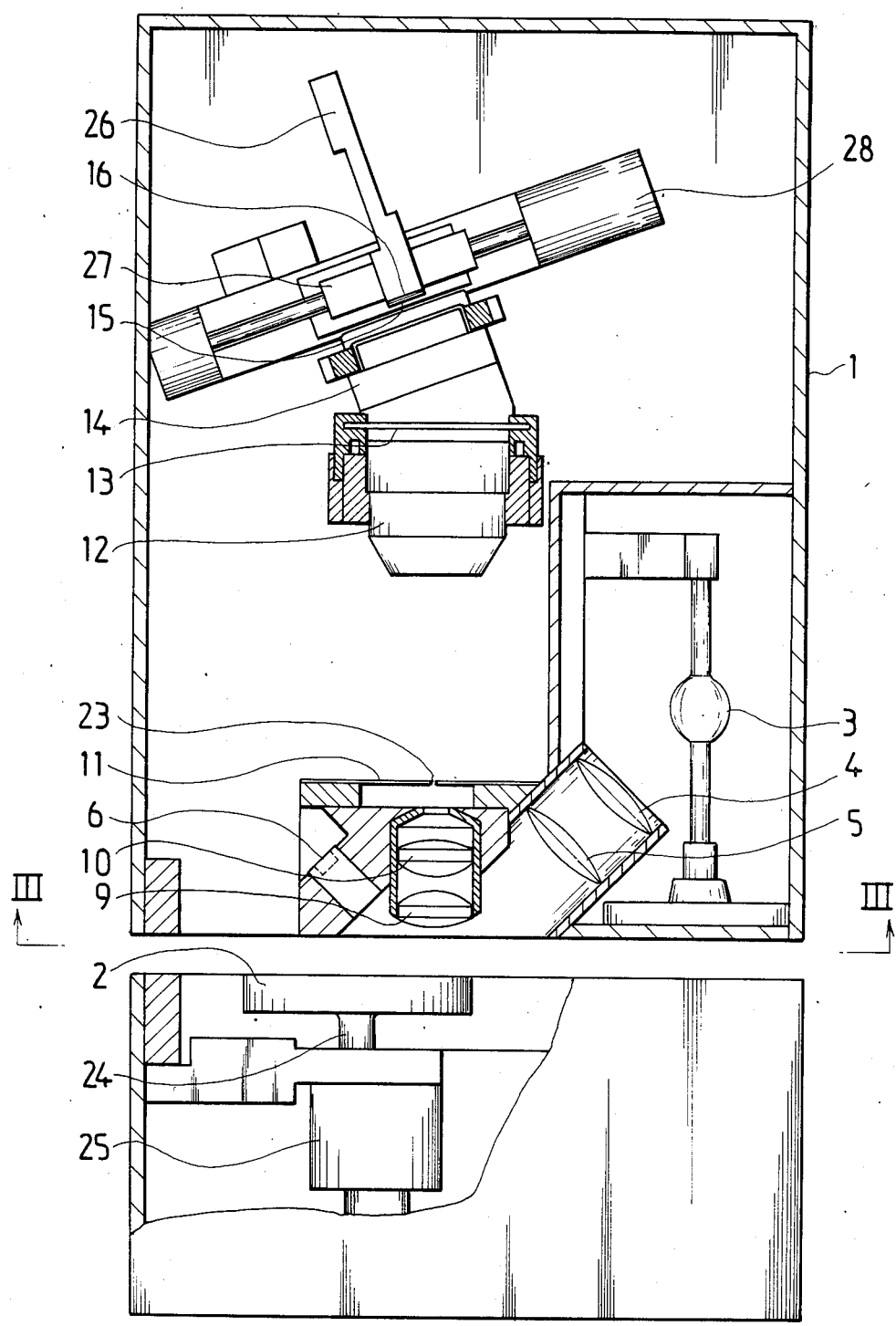
FIG. 1 shows a side view of one embodiment of an apparatus of the invention partially in cross-section.

The apparatus shown in FIG. 1 comprises a housing 1 and measuring, calibrating and monitoring equipment fitted inside the housing. Said housing is provided with openings for bringing paper in and out of the apparatus. A paper sample can be conveyed in the apparatus by means of its own conveyor means or the apparatus may operate as a component of a testing assembly, in which case paper will be conveyed by means of a conveyor of this assembly. The functions of the apparatus are monitored automatically by conventional means with the help of a computer and the results are displayed either by the apparatus' own output unit or the test assembly's output unit.

Figure 3:
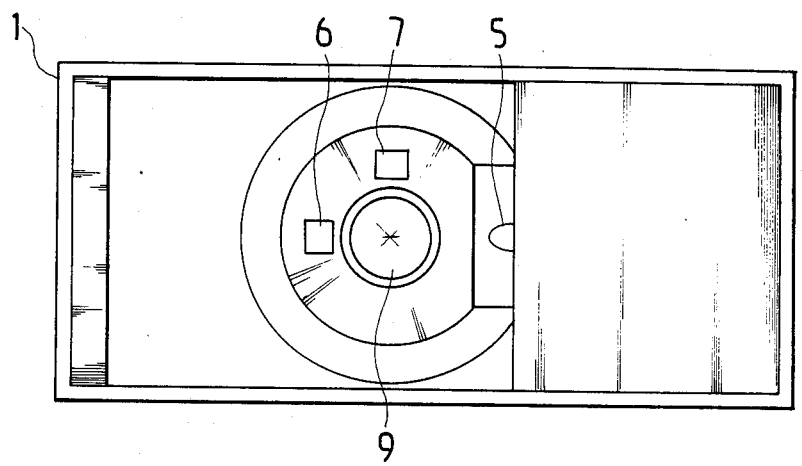
FIG. 3 shows the apparatus of FIG. 1 as seen from the direction III—III.

The apparatus is provided with a background screen 2 adapted to be movable relative to the housing, a light source 3 as well as lenses 4, 5, disposed between background screen and light source. The radiation center of the electric arc of a lamp is positioned so as to lie at the focal point of a converging lens 4. The converged light rays are parallel behind lens 4 and received by a lens 5 for focusing them further on a background screen or a paper sample. The light hitting a background screen or a paper sample reflects, scatters and penetrates through a sample. For measuring the reflected light, and as shown in FIG. 3, the apparatus is provided with two lateral detectors 6, 7, one detector 6 being positioned at the natural 45° angle of reflection of a light source and the other detector 7 being located at a position displaced 90° about the circumference of lense 9 from the position of detector 6 at a 45° angle of reflection relative to the plane of paper. The detectors 6 and 7 of FIG. 3 are preferably both photodiodes provided with an aperture tube used for selecting an angle of incidence and attenuation for the detector.

Figure 2:
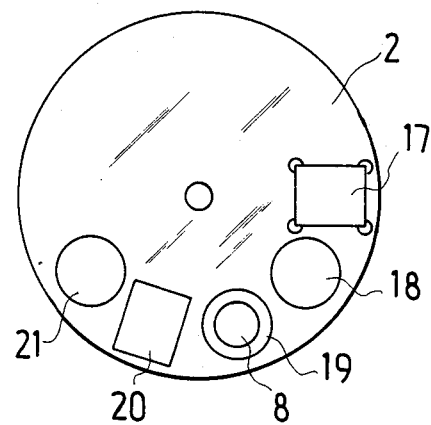
FIG. 2 shows one background screen of an apparatus of the invention in plan view.

As best seen in FIGS. 1 and 2, background screen 2 is a round disc shifted on a shaft 24 by means of a motor 25. Said background screen is provided equidistantly from the screen center with a mirror 17, a black base section 18, an aperture 19 through the screen, a white base section 20, as well as a black-walled aperture 21 through the screen, all these members serving as calibration and measuring means. The bottom of aperture 19 is fitted with a detector 8 for measuring the intensity of the light penetrated through paper. With the apparatus in measuring or calibrating position, said background screen is arranged in a manner that a calibrating or measuring element in question will be in register with the focal point of mirror 5. The operation of background screen will be detailed hereinbelow.

For collecting and focusing of scattered light, the apparatus is provided with lenses 9, 10, positioned above the focal point of lens 5. Lens 9 is used to converge the light to be measured and behind the lens the light rays extend parallel. Lens 10 receives the light and focuses it on the focal point. The apparatus is fitted with an aperture disc 11, positioned in a manner that the aperture 23 of aperture disc 11 is in register with the focal point of lens 10. The aperture diameter is circa 1 mm or less.

For converging the light emitting through aperture 23, the apparatus is provided with a collimator 12, comprising an array of collimation lenses with two duplex objective lenses one after the other. The collimator forwards the light as parallel rays to a grid 13. Grid 13 is positioned immediately adjacent to collimator optics. The light wave front meets the grid perpendicularly. After the grid, the various wavelengths of incoming light refract into different angles, in other words, light disperses into spectral elements.

The apparatus is further provided with an objective lens 14 fitted between grid 13 and detector 16 for focusing the spectrum of dispersed light into an image on the plane of detector screen. Thus, a line of focal points (spectrum) of wavelength groups arriving at various angles will be formed on the focal plane of this optics.

The apparatus comprises a detector 16 mounted on a holder 26 and a gap-equipped limiter 15 positioned immediately adjacent to said detector. Holder 26 is fastened to a base board 27, displaceable by means of a motor 28. Spectrum detector (16) consists of a base element mounted on the holder and a light-sensitive plane element. In this embodiment, the plane element is topped with a disc, serving as a limiter and having an approximately 0.6 mm wide gap at the center. The plane element of said detector is made higher than the height of a focused spectrum. Holder 26, along with its mounted spectrum detector 16, is conveyed on the above focal plane and in its immediate proximity step by step through the entire visible range of a spectrum, whereby it measures the intensity of a spectrum at a desired density. In addition to the visible spectral range, the detector can be moved for example, within the infrared zone of a spectrum for calibrating the detector position.

Figure 4:
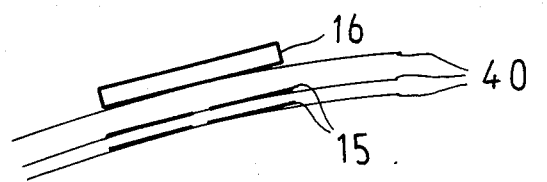
FIG. 4 shows, in part, a modified form of the apparatus of FIG. 1 incorporating a pair of limiter plates.
Figure 4:
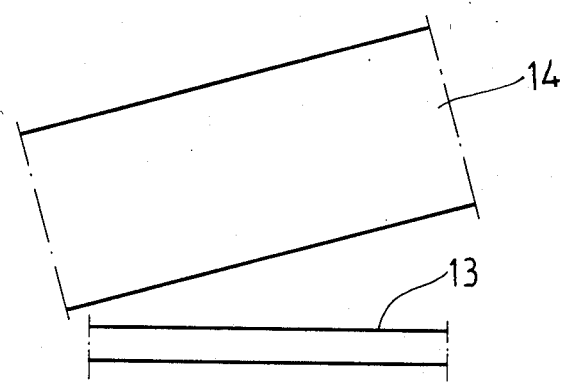

The modified apparatus of FIG. 4 includes a pair of limiters 15 positioned immediately adjacent to the spectrum detector 16 and between the grid 13 and objective lens 14 and the detector 16. The limiters 15, which function as a bandpass filter, and spectrum detector 16 are movable along a curved path 40 corresponding to the focal plane.

Figure 5:
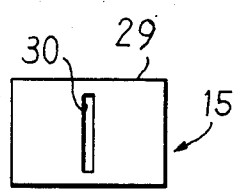
FIG. 5 shows a limiter plate in accordance with the invention.

A typical limiter 15 is illustrated in FIG. 5. A limiter plate 29 includes a substantially centrally-disposed gap 30 of predetermined width defined in and through the plate. The gap 30 limits the bandwidth of light passable therethrough and thereby enables the limiter 15 to function as a bandpass filter; the passband narrows as the width of the gap is decreased. It is therefore generally preferred that the gap be defined to be as narrow as reasonably possible. The apparatus described in this working example can be used to measure optical properties of paper, such as paper color, whiteness, opacity, gloss and transparency. The paper color is determined by first illuminating said white base section 20 of a background screen, which can be e.g. a $BaSO_4$-board, and by measuring relative intensities Iref at each analysed wavelength. This is followed by measuring from a sample corresponding relative intensities Ipap. The ratio Ipap/Iref corresponds to the relative light energy emitting from paper at each wavelength. The three-stimulus components X, Y and Z of paper color are calculated by means of the C.I.E. three-stimulus component curve by utilizing weighted value factors obtained from the curves at proper wavelengths. Then it is possible to determine the C.I.E. chromaticity coordinates X, Y and Z of the light emitted from a sample, so the color of paper can be displayed in a desired form after calculation.

The whiteness of paper is continuously measured on shifting paper in the apparatus, said spectrum detector 16 being used to compare the intensity of the 457 mm wavelength with the intensity provided by a reference surface (white) at the same wavelength.

Opacity is calculated from the measuring results of a stationary paper. The measuring detector is lateral detector 7. Capacity is Ipap. (black background)/Ipap. (white background).

The gloss of paper can be calculated in two ways from a moving paper: 1. gloss is Ipap (detector 6)/I mirror (detector 6). 2. gloss is I-Ipap (detector 7)/Ipap (detector 6).

Transparency is calculated from the results of penetration detector 8 and lateral detectors 7 as follows: 1. transparency is Ipap (detector 8)/Ipap (detector 7). 2. transparency is Ipap (detector 8)/mirror (detector 7).

The invention is by no means limited to the above embodiment but can be varied within the scope of the annexed claims.

We claim:

1. An apparatus for measuring optical properties of paper, said apparatus comprising a housing, a background screen for supporting a paper sample, and, inside said housing, a light source, lenses for focusing the light from said light source on the background screen, a plurality of first detectors for measuring the intensities of light reflected off paper on said screen and of light penetrating said paper, an assembly for processing scattered light, and a second detector for measuring the intensity of scattered light, characterized in that said background screen is movable relative to said housing and is provided with elements for measuring optical properties and calibrating the apparatus, and said assembly for processing scattered light comprises a grid and a pair of limiters positioned between said second detector and said grid in immediate proximity of said second detector, whereby said grid projects a sprectrum along a focal plane, said limiters comprising in conjunction with said grid a bandpass filter and being movable together with said detector within the range of a spectrum, along a curved path determined by the focal plane, said second detector being adapted to measure step by step the intensity of sections of desired width of the spectrum of light along the focal plane.

2. An apparatus as set forth in claim 1, characterized in that said apparatus comprises a lens fitted between said grid and detector for focusing a spectrum, the focal plane thus being provided with focal points corresponding to various wavelengths, said second detector being adapted to move on the focal plane and in its immediate proximity.

3. An apparatus as set forth in claim 1, comprising further lenses for converging and focusing scattered light, characterized in that said apparatus is provided with an aperture disc positioned in a manner so that an aperture of said aperture disc is in register with the focal point of at least one of said further lenses.

4. An apparatus as set forth in claim 3, characterized in that said apparatus is provided with a collimator positioned in a manner so that its focal point is in register with said aperture of said aperture disc and adapted to pass the light emitting through said aperture as parallel rays to said grid.

5. An apparatus as set forth in claim 1, characterized in that said background screen is provided equidistantly from the screen center with a mirror, a black base section, an aperture through said screen, a white base section, and a black-walled aperture through said screen, all these serving as calibration and measuring elements.

6. An apparatus as set forth in claim 2, comprising further lenses for converging and focusing scattered light, characterized in that said apparatus is provided with an aperture disc positioned in a manner so that an aperture of said aperture disc is in register with the focal point of at least one of said further lenses.

7. An apparatus as set forth in claim 6, characterized in that said apparatus is provided with a collimator positioned so that its focal point is in register with the aperture of said aperture disc and adapted to pass the light emitting through said aperture as parallel rays to said grid.

8. An apparatus as set forth in claim 2, characterized in that said background screen is provided equidistantly from the screen center with a mirror, a black base section, an aperture through said screen, a white base section, and a black-walled aperture through said screen, all these serving as calibration and measuring elements.

9. An apparatus as set forth in claim 3, characterized in that said background screen is provided equidistantly from the screen center with a mirror, a black base section, an aperture through said screen, a white base section, and a black-walled aperture through said screen, all these serving as calibration and measuring elements.

10. An apparatus as set forth in claim 4, characterized in that said background screen is provided equidistantly from the screen center with a mirror, a black base section, an aperture through said screen, a white base section, and a black-walled aperture through said screen, all these serving as calibration and measuring elements.

11. An apparatus as set forth in claim 5, characterized in that said background screen is provided equidistantly from the screen center with a mirror, a black base section, an aperture through said screen, a white base section, and a black-walled aperture through said screen, all these serving as calibration and measuring elements.

12. An apparatus as set forth in claim 6, characterized in that said background screen (2) is provided equidistantly from the screen center a mirror (17), a black base section (18), an aperture (19) through said screen, a white base section (20), and a black-walled aperture (21) through said screen, all these serving as calibration and measuring elements.

* * * * *